United States Patent [19]

Ianniruberto et al.

[11] Patent Number: 5,226,890
[45] Date of Patent: Jul. 13, 1993

[54] TISSUE GRIPPING DEVICE

[75] Inventors: Alex Ianniruberto, Waterbury, Conn.; Michael Ciccolella, Lake Carmel, N.Y.

[73] Assignee: United States Surgical Corporation, Norwalk, Conn.

[21] Appl. No.: 792,028

[22] Filed: Nov. 13, 1991

[51] Int. Cl.⁵ .......................................... A61M 5/32
[52] U.S. Cl. ................................ 604/164; 604/174; 604/178
[58] Field of Search ............ 604/164, 165, 171, 174, 604/175, 178, 264, 272

[56] References Cited

U.S. PATENT DOCUMENTS

| | | | |
|---|---|---|---|
| 695,470 | 3/1902 | Milam | 604/42 |
| 2,185,927 | 1/1940 | Shelanski | |
| 2,256,942 | 9/1941 | Duffy | |
| 2,496,111 | 1/1950 | Turkel | |
| 2,623,521 | 12/1952 | Shaw | |
| 3,039,468 | 6/1962 | Price | |
| 3,241,554 | 3/1966 | Coanda | |
| 3,253,594 | 5/1966 | Matthews et al. | |
| 3,459,175 | 8/1969 | Miller | |
| 3,515,137 | 6/1970 | Santomieri | 604/165 |
| 3,613,684 | 10/1971 | Sheridan | |
| 3,750,667 | 8/1973 | Pshenicnhy et al. | |
| 3,789,852 | 2/1974 | Kim et al. | 128/347 |
| 3,817,250 | 6/1974 | Weiss et al. | 128/305 |
| 3,817,251 | 6/1974 | Hasson | 128/348 |
| 3,860,006 | 1/1975 | Patel | 128/347 |
| 3,993,079 | 11/1976 | Gatztanondo | 128/347 |
| 4,077,412 | 3/1978 | Moossun | 128/347 |
| 4,186,750 | 2/1980 | Patel | 128/748 |
| 4,215,699 | 8/1980 | Patel | 128/748 |
| 4,627,838 | 12/1986 | Cross et al. | 604/105 |
| 4,668,222 | 5/1987 | Poirier | 604/175 |
| 4,670,008 | 6/1987 | Von Albertini | 604/165 |
| 4,755,173 | 7/1988 | Konopka et al. | 604/167 |
| 4,772,261 | 9/1988 | Von Hoff et al. | 604/175 |
| 4,894,052 | 1/1990 | Crawford | 604/165 |
| 4,976,697 | 12/1990 | Walder et al. | 604/164 |
| 5,002,557 | 3/1991 | Hasson | 606/191 |
| 5,112,321 | 5/1992 | Hiltebrandt | 604/264 |

FOREIGN PATENT DOCUMENTS 0413493 2/1991 European Pat. Off. .
475215 10/1952 Italy .

OTHER PUBLICATIONS

Enopath Brochure of Ethicon, Inc.
1988 Orthopaedics Richards Annual Product Catalog.
Bone Screw Technical Information Brochure of Richards Manufacturing Company, Inc.
Auto Suture Surgigrip TM Brochure of United States Surgical Corporation.
"A Modified Instrument and Method for Laparoscopy"; Communications in brief, 1971 886–887.

*Primary Examiner*—John G. Weiss
*Attorney, Agent, or Firm*—Thomas R. Bremer; Peter G. Dilworth; Rocco S. Barrese

[57] ABSTRACT

An apparatus for maintaining a positional relationship between a trocar cannula and body tissue into which the cannula is inserted includes a tissue engaging member having a conical outer surface with a thread helically disposed thereon. A guide tube is insertable into a bore in the tissue engaging member, the guide tube having a camming surface. A collet with flexible projections is engageable with the guide tube. When the collet is tightened onto the guide tube the flexible projections bend inward to frictionally engage and hold a trocar cannula inserted through the axial bore of the apparatus.

21 Claims, 4 Drawing Sheets

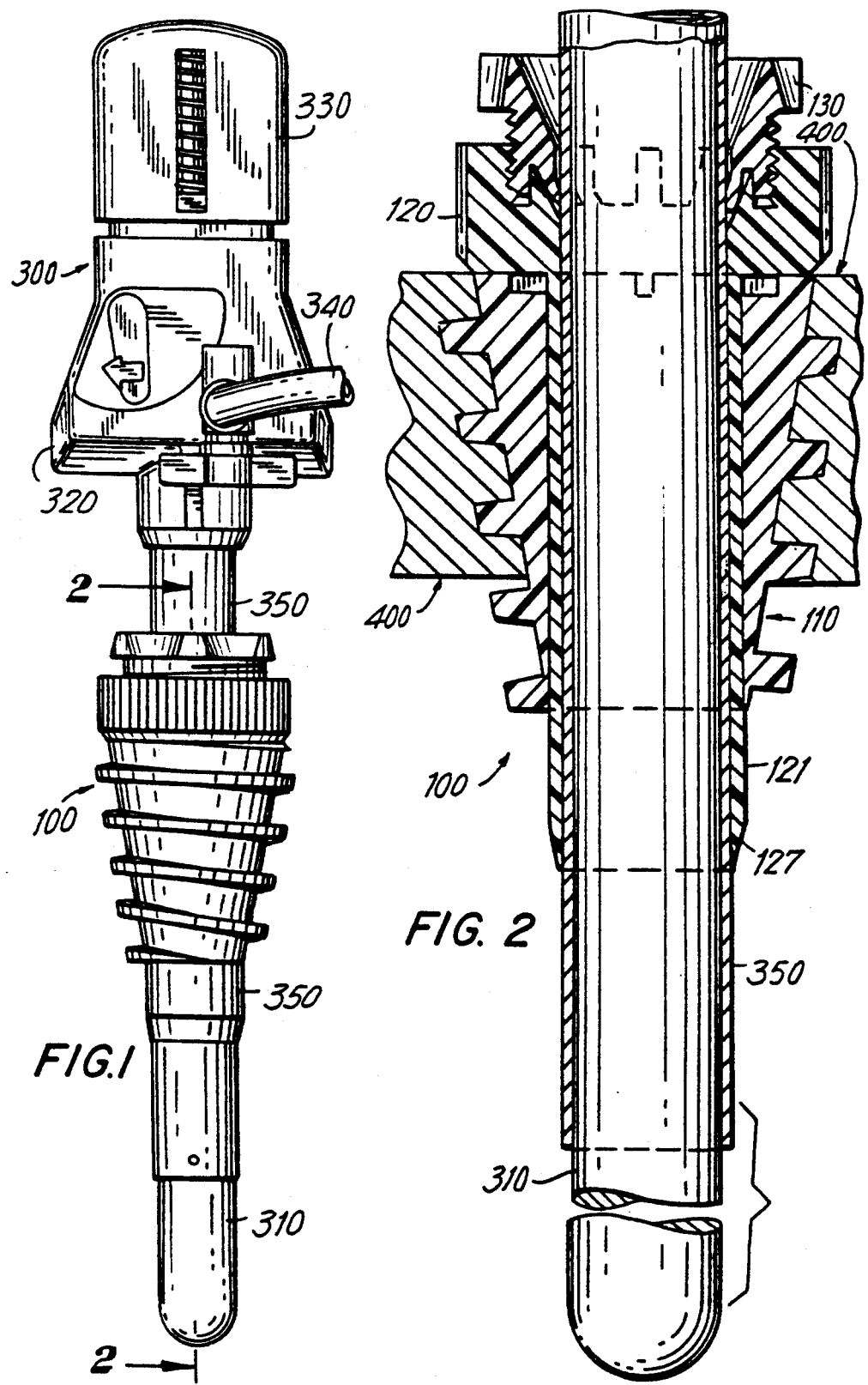

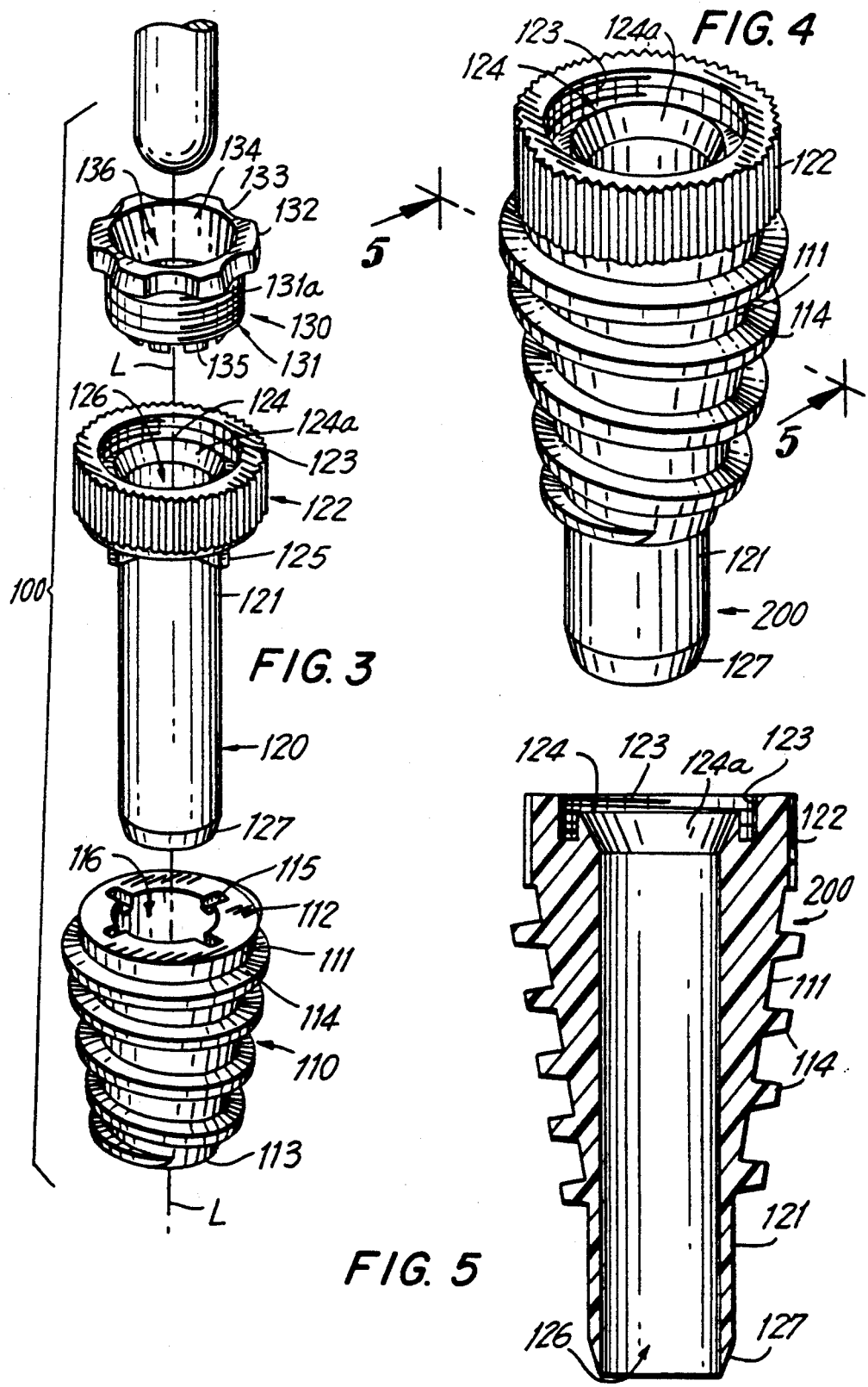

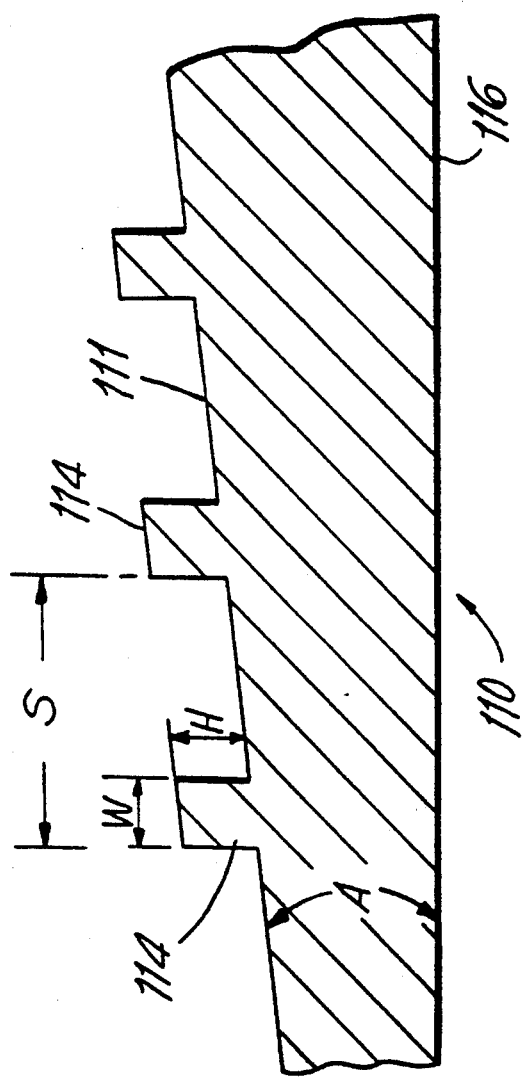

TISSUE GRIPPING DEVICE

BACKGROUND OF THE INVENTION

1. Field of the Invention

The present invention relates to a device for retaining a medical instrument in engagement with body tissue and, more particularly, to an improved device for maintaining the desired positional relationship between a trocar tube and body tissue.

2. Background of the Related Art

Devices for holding medical instruments in penetrating relationship with body tissue are known. See, for example, U.S. Pat. No. 2,256,942 which discloses an instrument having a fluted or undulated surface for retaining the device in the walls of the bladder or viscus; U.S. Pat. No. 3,750,667 which discloses a device having a thread which serves to measure the depth of introduction of the device into osseous tissue; and U.S. Pat. No. 4,670,008 which discloses a high flux threaded needle for injecting or removing fluids from the body, the needle having a threaded portion to permit easy insertion of the needle and secure the device in the patient.

Threaded structures have also been applied to larger diameter trocars which are used for introducing viewing and surgical instruments into the body. Such trocars are shown and described in U.S. Pat. Nos. 4,601,710; 4,654,030, and 4,902,280. One commercially available trocar includes a cannula having an integrally molded threaded portion for holding the cannula in the patient's skin. Another device marketed under the trademark SURGIGRIP by U.S. Surgical Corporation, Norwalk, Conn., provides a depth penetration indicator adjustable to a desired position along a cannula and including a threaded portion for holding the cannula in the patient's skin.

Such devices are especially useful in open laparoscopy procedures wherein a surgeon inserts a cannula into an opening in body tissue made with a scalpel. The scalpel-made opening may have a greater tendency to leak gas and/or fluid from around the cannula than does a trocar created opening.

SUMMARY OF THE INVENTION

An apparatus is provided herein for maintaining a positional relationship between an elongated surgical instrument and body tissue into which the surgical instrument is inserted. The apparatus includes first means at least partially insertable into an opening in the body tissue, and, associated with the first means, second means possessing a conical surface having disposed thereon at least one thread for engaging the edges of the opening in the body tissue. More particularly, the apparatus includes a first member for insertion into an opening in a wall of body tissue, the first member having distal and proximal ends, a camming surface, a cylindrical tube portion, and an axial bore configured and dimensioned to receive the elongated surgical instrument. Also included are tissue engaging means in conjunction with the first member, the tissue engaging means having a conical outer surface and at least one tissue engaging thread helically disposed around the conical surface. A second member is provided which includes collet means adapted to cooperate with the first member and having an axial bore configured and dimensioned to receive the elongated surgical instrument. The collet means is movable with respect to the first member to a position wherein projections associated with the collet means engage the camming surface of the first member and are moved radially inward to frictionally engage and hold the elongated surgical instrument when positioned within the axial bore.

BRIEF DESCRIPTION OF THE DRAWINGS

FIG. 1 is an elevational view of the tissue gripping device of the present invention in conjunction with a trocar assembly.

FIG. 2 is a sectional view of the tissue gripping device inserted into body tissue.

FIG. 3 is an exploded perspective view of the tissue gripping device.

FIG. 3a illustrates a sectional view of the threads of the conical tissue engager.

FIGS. 4 and 5 are perspective and sectional views, respectively, of an alternative embodiment of the threaded conical portion of the tissue gripping device.

DETAILED DESCRIPTION OF PREFERRED EMBODIMENTS

Figure 3B:
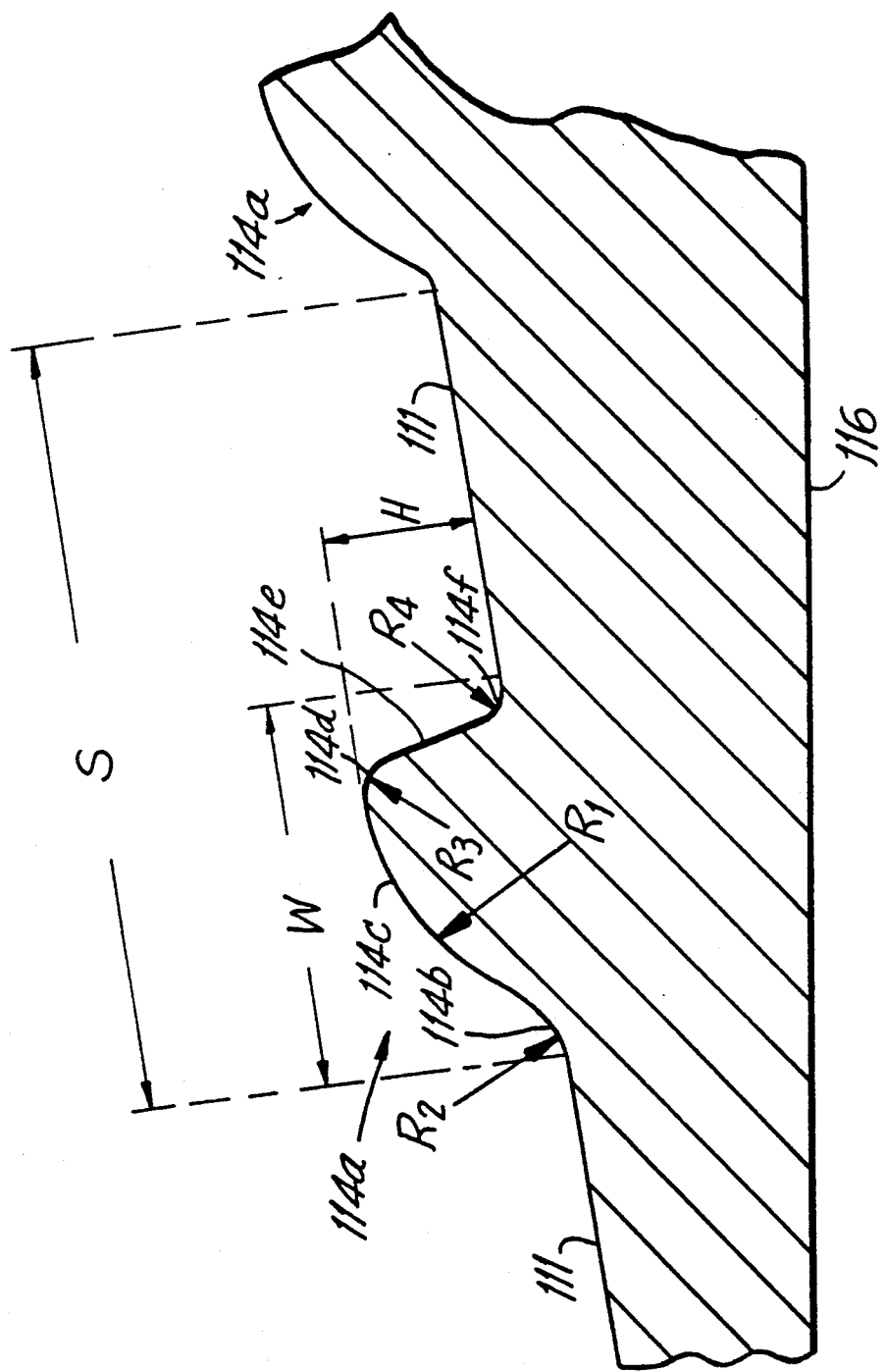
FIG. 3b illustrates a sectional view of an alternative thread configuration for the conical tissue engager.

The tissue gripping device of the present invention is intended to be used in conjunction with a trocar assembly during laparoscopic, and particularly open laparoscopic, procedures. The trocar assembly can be of known design and may have either a sharp pointed obturator or a blunt obturator.

Referring to FIG. 1, a trocar assembly 300 having obturator 310 mounted to obturator housing 330, and cannula 350 mounted to cannula housing 320 is employed in conjunction with tissue gripping device 100. The cannula 350 is disposed through an axially extending bore in the tissue gripping device 100 and the obturator 310 is disposed through the axial bore of the cannula 350. A tube 340 provides means for communicating a gas to or from the interior of the body cavity penetrated by the cannula.

FIG. 2 illustrates a sectional view of the tissue gripping device implanted into a body through a wall of tissue 400. Referring to FIGS. 2 and 3, the tissue gripping device 100 includes a threaded conical tissue engager 110, a tubular guide member 120, and a locking collet 130.

More particularly, the tissue engager 110 includes a thread 114 extending helically around a conically shaped outer surface 111 from the proximal end 112 to the distal end 113 of the tissue engager 110. A cylindrical bore 116 extends axially through the tissue engager 110 and is adapted to receive cylindrical tube 121 of tubular guide 120. Notches 115 extend radially along the proximal end 112 of the tissue engager 110 and are adapted to receive corresponding detents 125 in the tubular guide 120.

Referring to FIG. 3a, the thread height H, thread width W, thread spacing S, and angle A of the conical surface 111 are chosen so as to provide optimum entry and removal force and fluid sealing with minimum tissue trauma, and sufficient holding power to retain the laparoscopic instrumentation in the desired position. Typically, the thread height H can be from about 0.005 to 0.1 inches; thread width W can be from about 0.02 to 0.15 inches; thread spacing S can be from about 0.1 to 0.3 inches; and angle A between the surface of bore 116 and the conical surface 111 can be from about 5 degrees to about 45 degrees.

Referring to FIG. 3b, an alternative thread shape is illustrated in sectional view. The thread 114a has a distal sloping surface 114c extending from a curved distal foot region 114b to a curved thread apex 114d disposed radially outward of surface 111. Distal sloping surface 114c preferably is curved and has a radius $R_1$ in the range of about 0.07 to 0.09 inches, and most preferably has a radius of about 0.08 inches. Curved distal foot region 114b is connected to and extends from base surface 111 to join sloping surface 114c to the base surface 111. Curved distal foot region 114b should have a radius $R_2$ in the range of about 0.01 to 0.03 inches, and preferably has a radius of about 0.02 inches. Thread 114a also has a proximal end wall 114e substantially perpendicular to base surface 111 extending from a proximal foot region 114f to thread apex 114d. Thread apex 114d preferably defines a curved surface connecting distal sloping surface 114c to proximal end wall 114e. The curve of thread apex 114d preferably defines a radius $R_3$ of about 0.01 inches. Proximal foot region 114f joins proximal end wall 114e to base surface 111, and preferably is a curved surface defined by a radius $R_4$ of about 0.01 inches. The total longitudinal thread width W is measured from the point where distal curved foot region 114f joins base surface 111 to the point where proximal curved foot region 114 joins base surface 111. For tissue such as skin, the thread width W should be about 0.10 to 0.11 inches and the thread height H should be about 0.08 to 0.09 inches. It has also been found that for skin tissue the optimum longitudinal thread spacing "S" along base surface 111 should be about 0.275 to 0.300 inches, and most preferably is about 0.285 inches.

Referring again to FIG. 3 the tubular guide 120 includes a tubular shaft portion 121 having an exterior diameter adapted to fit into bore 116 in the conical tissue engager 110. The inner diameter of axial bore 126 in the guide 120 is of such dimension to accommodate a cannula of a trocar assembly (See, e.g. FIG. 1). The distal end 127 of tubular shaft 121 preferably is beveled to facilitate its insertion into bore 116. The distal portion of guide 120 includes a knob 122 with a knurled circumferential surface. At the distal surface of the knob detents 125 are positioned in radial orientation, the detents being dimensioned and configured so as to fit into the corresponding notches 115 of the tissue engager 110. The inner surface 123 of the knob 122 is threaded. Proximally extending camming ridge 124 extends circumferentially around the proximal opening of bore 125 and possesses an inwardly sloped camming surface 124a defining an angle of about 20° to about 25° relative to the longitudinal axis L of guide 120.

The collet 130 is a generally cylindrical member which comprises distal tube portion 131 with a threaded outer surface, 131a. A plurality of flexible locking projections 135 extend distally and generally longitudinally in a circumferential pattern around the distal opening of axial bore 136. The threaded tube portion 131 is adapted to screw into the proximal end, i.e. the knurled knob, of the tubular guide 120, whereupon the locking projections 135 engage sloped surface 124a of the ridge 124 and are cammed radially inwardly to frictionally engage a trocar cannula or other such implement positioned within the bore.

The proximal end of the collet 130 includes a circumferential ridge 132 with depressions 133 for accommodating the fingers of a user. The proximal end 134 of bore 36 is sloped so as to facilitate insertion therethrough of a trocar cannula, obturator, or other laparoscopic instrument.

Referring to FIG. 2, the tubular guide 120 is inserted into the tissue engager 110 such that detents 125 engage notches 115. Thus, rotation of the knurled knob 122 causes rotation of the tissue engager 110. The collet 130 is screwed part way into the proximal opening of the guide 120.

After a surgeon has created an incision, for example, in the skin 400, the assembly 100 is inserted into the incision and the knurled knob 122 is rotated counterclockwise so as to screw tissue engager 110 into the incision. A trocar cannula 350 and obturator 310 are inserted through the axial bore of the collet 130 and the guide 120. When the surgeon is satisfied with the positioning of the cannula 350, the collet 130 is turned so as to hold cannula 350 in place by means of cammed projections 135. The guide 120 is disengageable from gripper 110 by lifting it out from slots 115. Thus, fitting 120 can be rotated independently of tissue engager 110.

Referring to FIGS. 4 and 5, an alternative embodiment of the invention is shown wherein the tissue engager and the tubular guide are integrated in a single piece 200. Thus, integrated piece 200 has a tubular portion 121 with distal bevelled edge 127, conical surface 111 with threads 114, knurled knob 122 with threaded inner surface 123, proximally extending camming ridge 124 with sloped camming surface 124a and axial bore 126. The detents 125 and notches 115 are not employed with integrated piece 200.

The individual pieces of the gripping assembly 100 may be molded from a synthetic polymer such as glass filled acetal or polycarbonate. In a preferred embodiment, the tubular guide 120 and tissue engager 110 are constructed of glass-filled acetal and locking member 130 is constructed of polycarbonate. The preferred acetal material is available from LNP Division of ICI America Inc. under the trade specification KFL 4023, and the preferred polycarbonate material is available from General Electric Company under the trade name LEXAN. The preferred acetal-polycarbonate arrangement reduces binding at the threaded engagement of the tubular guide 120 and collet 130 threaded sections. Of course, the same result may be obtained by constructing the tubular guide 120 of polycarbonate and the collet 130 of acetal, but an acetal collet may slide on a metal cannula or guide tube.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. An apparatus for maintaining a positional relationship between an elongated surgical instrument and body tissue into which the surgical instrument is inserted, which comprises:

first means at least partially insertable into an opening in the body tissue and having a bore for providing access for the surgical instrument to the interior of the body, and, associated with said first means, second means possessing a conical surface having disposed thereon at least one thread for engaging the edges of the opening in the body tissue; and wherein said second means is detachable from said first means.

2. The apparatus of claim 1, wherein said thread is helical.

3. The apparatus of claim 1 further including third means removably engageable with said first means and movable to a locking position for frictionally engaging said surgical instrument when said surgical instrument is positioned within the bore of said first means.

4. The apparatus of claim 3, wherein said third means comprises a collet member which possesses threads for screw engagement with said first means, and wherein said collet includes a plurality of resilient distally pointing projections which are engageable with a camming surface on said first member when said third means is moved to said locking position, said projections thereby being radially inwardly biased to a position for frictionally engaging the surgical instrument.

5. An apparatus for maintaining a positional relationship between an elongated surgical instrument and body tissue into which the surgical instrument is inserted, which comprises:
a) a first member for at least partial insertion into an opening in a wall of body tissue, said first member having distal and proximal ends, inwardly directed camming means, a cylindrical tube portion, and an axial bore extending therethrough, said first member being configured and dimensioned to receive the elongated surgical instrument, and further having tissue engaging means removably attachable to said cylindrical tube portion and having a conical outer surface and at least one tissue engaging thread helically disposed around said conical surface; and
b) a second member comprising collet means adapted to cooperate with said first member and having an axial bore configured and dimensioned to receive the elongated surgical instrument, said collet means being movable with respect to said first member to a position such that said camming means cooperates with said collet means to frictionally engage and hold the elongated surgical instrument within said axial bore.

6. The apparatus of claim 5, wherein said collet means includes a plurality of projections disposed around one opening of the bore in the collet means.

7. The apparatus of claim 5, wherein said first member includes a knob having an outer diameter wider than that of the cylindrical tube portion, said knob being at the proximal end of the first member and having a circumferential outer surface for contact by the fingers of a user for rotating said first member.

8. The apparatus of claim 7, wherein said knob has a distal surface including at least one detent projecting distally therefrom.

9. The apparatus of claim 7, wherein said knob has a threaded inner surface for receiving a corresponding threaded outer surface of the collet means.

10. The apparatus of claim 7, wherein said camming surface extends circumferentially around the proximal opening of the bore of the first member and is inclined at an angle of from about 20° to about 25° from the longitudinal axis of the bore.

11. The apparatus of claim 5, wherein said first member includes a knob portion fixedly positioned at the proximal end of the cylindrical tube portion, said knob portion having a circumferential outer surface for contact by the fingers of a user for rotating said first member, and a proximal surface for abutting a distal surface of said conical portion, said apparatus possessing means for engaging said knob portion and said conical portion.

12. The apparatus of claim 11, wherein said means for engaging said knob portion and said conical portion comprises at least one detent in one of said proximal surface of the knob portion and distal surface of the conical portion, and a corresponding and cooperating at least one notch in the other of said proximal surface of the knob portion and distal surface of the conical portion.

13. The apparatus of claim 5, wherein the conical outer surface of the tissue engaging means is configured at an angle of from about 5 degrees to about 45 degrees from the longitudinal axis of the bore.

14. The apparatus of claim 5, wherein the height of the tissue engaging thread is from about 0.005 inches to about 0.1 inches, the thread width is from about 0.15 inches to about 0.20 inches, and the thread spacing is from about 0.1 inches to about 0.3 inches.

15. An apparatus for maintaining a positional relationship between an elongated surgical instrument and body tissue into which the surgical instrument is inserted, which comprises:
a) a first member for insertion into an opening in a wall of body tissue, said first member having distal and proximal ends, a camming surface, a cylindrical tube portion, an axial bore configured and dimensioned to receive the elongated surgical instrument, and a knob having an outer diameter wider than that of the cylindrical tube portion, said knob being at the proximal end of the first member and having a circumferential outer surface for contact by the fingers of a user for rotating said first member, a threaded inner surface, and a distal surface including at least one detent projecting distally therefrom;
b) tissue engaging second member engageable with said first member, said tissue engaging second member having an axial bore adapted to receive said cylindrical tube portion of the first member, said second member having a conical outer surface and at least one tissue engaging thread helically disposed around said conical surface, and said second member further having a proximal end with a diameter relatively wider than the distal end, and including a proximal end with a diameter relatively wider than the distal end, and including at least one notch in the proximal end, said notch being configured and dimensioned to receive said at least one detent of said knob; and
c) collet means connectable with said first member and having an axial bore configured and dimensioned to receive the elongated surgical instrument, and a plurality of distally extending projections disposed around the distal opening of said axial bore of the collet means, said collet means having an outer threaded surface which is engageable with the inner threaded surface of the knob, the collet means being movable with respect to said first member to a position wherein said projections engage the camming surface of said first member and are moved radially inward to frictionally engage and hold the elongated surgical instrument when positioned within said axial bore.

16. An apparatus for maintaining a positional relationship between an elongated surgical instrument and body tissue into which the surgical instrument is inserted, which comprises:

first means at least partially insertable into an opening in the body tissue and having a bore for providing access for the surgical instrument to the interior of the body, and, associated with said first means, second means possessing a conical surface having disposed thereon at least one thread for engaging the edges of the opening in the body tissue wherein said second means is detachable from said first means.

17. An apparatus for maintaining a positional relationship between a cannula and body tissue through which the cannula extends, said cannula adapted to receive an obturator which comprises:

a body portion at least partially insertable into an opening in the body tissue, said body portion having a bore for providing access for the cannula to the interior of the body, and a detachable member having a conical exterior surface with at least one thread for engaging the body tissue adjacent the body opening.

18. The apparatus of claim 17, wherein said apparatus body portion has a proximal and a distal end and wherein said distal end is beveled.

19. The apparatus of claim 17, wherein said apparatus body portion is adapted to be releasably secured to said cannula in a desired position relative to said cannula.

20. The apparatus of claim 19, wherein said apparatus further comprises means associated with said instrument body portion to releasably secure said apparatus body portion to said cannula.

21. The apparatus of claim 17, wherein said obturator is selected from the group consisting of a sharp pointed obturator and a blunt obturator.

* * * * *